United States Patent [19]

Blaha et al.

[11] Patent Number: 5,071,246
[45] Date of Patent: Dec. 10, 1991

[54] CONFOCAL SCANNING OPHTHALMOSCOPE

[75] Inventors: Erich Blaha, Essingen; Gerhard Gaida, Aalen, both of Fed. Rep. of Germany

[73] Assignee: Carl-Zeiss-Stiftung, Heidenheim, Fed. Rep. of Germany

[21] Appl. No.: 603,210

[22] Filed: Oct. 25, 1990

[30] Foreign Application Priority Data

Oct. 27, 1989 [DE] Fed. Rep. of Germany ... 8912757[U]

[51] Int. Cl.$^5$ .............................................. A61B 3/10
[52] U.S. Cl. ...................................... 351/221; 351/205
[58] Field of Search ....................... 351/205, 214, 221; 606/4

[56] References Cited

U.S. PATENT DOCUMENTS 3,698,099 10/1972 Matsura .
4,702,576 10/1987 Magnante ............................ 351/221
4,711,542 12/1987 Ichihashi et al. .
4,886,351 12/1989 Sabban et al. .

Primary Examiner—Rodney B. Bovernick
Attorney, Agent, or Firm—Walter Ottesen

[57] ABSTRACT

The invention is directed to a confocal scanning ophthalmoscope defining an illuminating beam path and a viewing beam path with these paths having respective portions extending along a common path segment. The ophthalmoscope has a light-deflecting device mounted in a first apparatus part and in the common path segment for scanning the ocular fundus point-by-point. A first flexible light-wave conductor conducts light transmitted by a real light source to a point light source. The ophthalmoscope has a pinhole diaphragm which is mounted in the viewing beam path and in a plane conjugated to the point light source. A detector of the ophthalmoscope measures the light transmitted through the pinhole diaphragm and a second flexible light-wave conductor conducts this light to the detector. The detector is mounted in a second apparatus part separate from the first apparatus part so as to permit movement of the parts relative to each other.

6 Claims, 2 Drawing Sheets

Fig.2

CONFOCAL SCANNING OPHTHALMOSCOPE

FIELD OF THE INVENTION

The invention relates to a confocal scanning ophthalmoscope having a single light-deflecting device for scanning the ocular fundus point-by-point with the light of a point light source. The light-deflecting device is mounted in a common portion of the illuminating and viewing beam path. A flexible light conductor is provided which conducts the light to the point light source with the light being transmitted from a real light source. The confocal scanning ophthalmoscope further includes a pinhole diaphragm which is mounted in the viewing beam path in a plane conjugated to the point light source and further includes a detector for measuring the light transmitted through the pinhole diaphragm.

BACKGROUND OF THE INVENTION

A scanning ophthalmoscope of the kind described above is disclosed in U.S. Pat. No. 4,886,351. This ophthalmoscope operates to examine the ocular fundus with a high resolution. For this purpose, the beam path of a point light source is deflected in a scan-like manner with the aid of a light-deflecting device and is imaged on the ocular fundus. The light reflected at the ocular fundus transilluminates the same light-deflecting device in the opposite direction and is thereafter deflected by a beam splitter into the viewing beam path.

A pinhole diaphragm is provided in the viewing beam path in a plane conjugated to the plane of the point light source to improve the contrast and the resolution. A detector detects the light transmitted through the pinhole diaphragm. The diameter of the pinhole diaphragm is so selected that only the light reflected at the ocular fundus reaches the detector. The output signal of the detector is conducted to an image memory and a monitor which is synchronized with the light-deflecting device and thereby provides a television image of the illuminated region of the eye.

The point light source can be realized by the beam waist of a focussed laser beam. A light-wave conductor can be mounted between the laser and the objective generating the waist of the laser beam for providing a physical separation between the laser and that part of the ophthalmoscope which is disposed in the proximity of the patient. In this way, a compact configuration of that part of the apparatus which is to be aligned to the eye of the patient is possible.

The light-deflecting device comprises a mirror-wheel scanner and a galvano scanner and, with this ophthalmoscope, the light-deflecting device generates electromagnetic stray fields. Because of the spatial proximity between the deflecting device and the detector, the electromagnetic stray fields can easily lead to interference signals at the output of the detector and in the signal processing downstream of the detector. Complex screening measures are required to prevent such interference signals.

The detector is a photomultiplier in ophthalmoscopes which are especially light sensitive. Since the photomultiplier is driven at a high voltage of approximately 1000 volts, very costly protective measures must be taken for reasons of apparatus safety. These protective measures furthermore require a great deal of space.

A very compact configuration of such an ophthalmoscope is on the other hand desirable since the person conducting an examination must align the ophthalmoscope with the eye of the patient in that the examining person looks at the eye of the patient laterally of the ophthalmoscope and views the light spot generated there by the ophthalmoscope. A compact configuration of the ophthalmoscope therefore makes possible a comfortable and rapid alignment of the ophthalmoscope with the eye of the patient.

SUMMARY OF THE INVENTION

It is an object of the invention to provide an ophthalmoscope of the kind described above wherein the part thereof to be aligned with the eye of the patient is more compact than in known apparatus. It is another object of the invention to provide an ophthalmoscope wherein the occurrence of interference signals as a consequence of stray fields generated by the light-deflecting device is prevented so that they do not interfere in the electronic data lines.

According to a feature of the invention, a second flexible and multimode light-wave guide is provided between the pinhole diaphragm and the detector. Also, the detector is mounted in a separate part of the apparatus which is movable relative to the part of the apparatus containing the light-deflecting device.

The second light-wave conductor permits the light to be conducted over a longer distance which can possibly amount to several meters. The stray fields of the light-deflecting device are hardly visible with this distance. When the ophthalmoscope is aligned to the eye of the patient, it is not necessary to align the detector therewith because the light-wave conductor is flexible. The detector is instead mounted in a separate housing which is stationary during examination. The part of the ophthalmoscope to be aligned with the eye of the patient can then be configured to be correspondingly more compact.

If the detector is a photomultiplier, danger to the patient or to the person conducting the examination is prevented by the spatial separation between the photomultiplier and the part of the apparatus to be aligned with the eye of the patient. Expensive measures which take up space are therefore not required.

The use of glass fibers for transmitting images is known from the ophthalmic apparatus disclosed in U.S. Pat. Nos. 3,698,099 and 4,711,542. However, the glass fibers disclosed in these patents are provided simply to transmit the image or the back-scattered light via a flexible optical path. In contrast, these patents do not disclose how interference signals emanating from a light-deflecting device can be prevented from straying into the data lines. Furthermore, the ophthalmic apparatus described are not scanning ophthalmoscopes.

It is advantageous when the light source and the detector conjointly define a spatial unit wherein the electronic signal processing can also be accommodated. The ophthalmoscope includes then a first apparatus part to be aligned with the eye of the patient and a second apparatus part which is stationary.

The light-wave conductor between the pinhole diaphragm and the detector is advantageously provided to be multimode. Such a multimode wave conductor is thicker and therefore not quite as sensitive to adjustment as a monomode wave conductor. The core diameter of the light-wave conductor should be greater than the diameter of the pinhole diaphragm so that the largest possible portion of the light transmitted through the pinhole diaphragm is coupled into the light-wave conductor.

The core of the light-wave conductor can however itself constitute the pinhole diaphragm. In this case, the core diameter of the light-wave conductor should correspond to the diameter of the pinhole diaphragm which is then not necessary.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
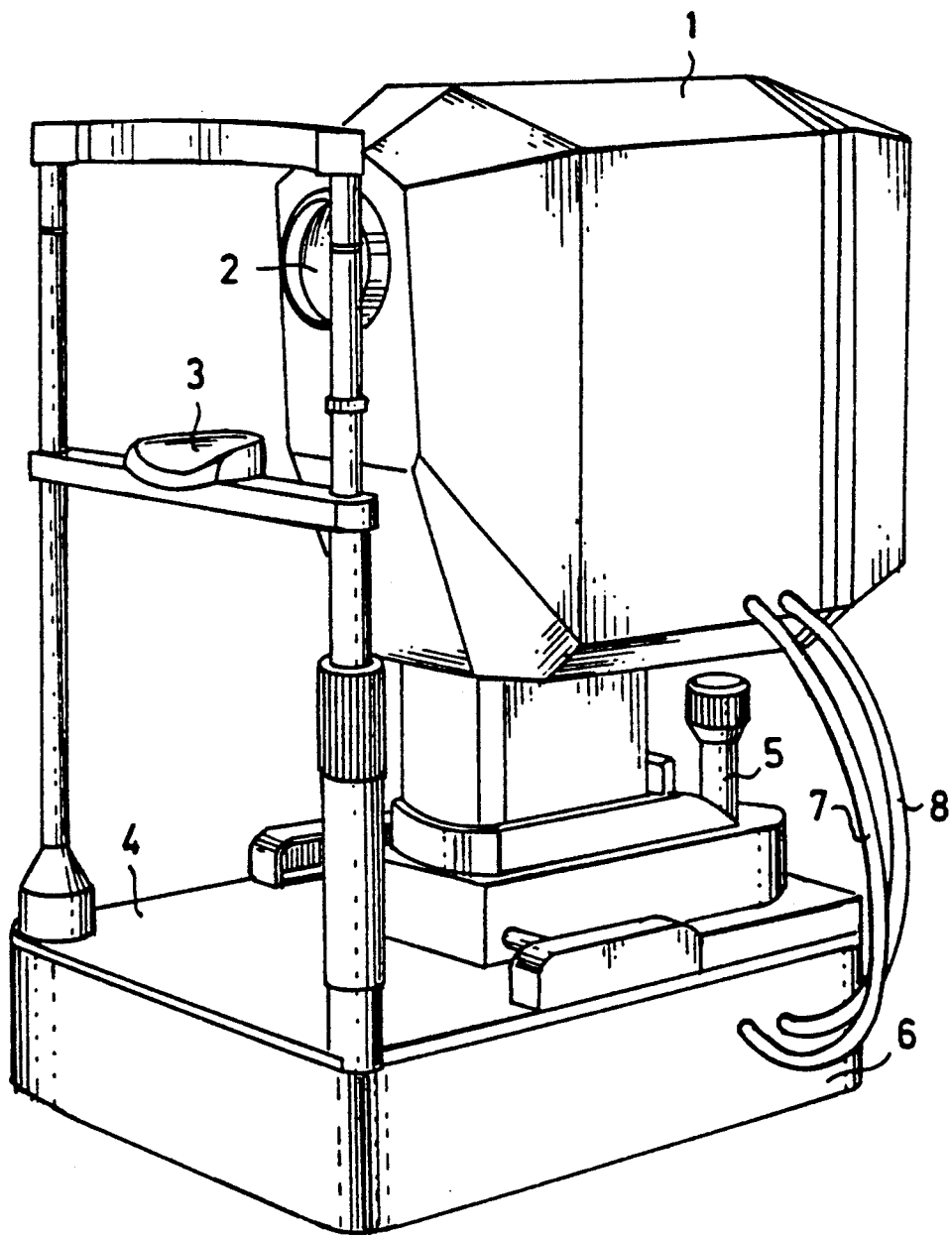
FIG. 1 is a perspective view of a confocal scanning ophthalmoscope according to the invention; and, FIG. 2 is a schematic of the beam path in a confocal scanning ophthalmoscope according to the invention.

In FIG. 1, the upper part of a confocal scanning ophthalmoscope is identified by reference numeral 1. A laser beam emanates from this upper part 1 through an opening 2. The laser beam is focussed into the eye of a patient. A chin support 3 is provided to stabilize the head of the patient. The chin support is mounted on a base plate 4 so as to be adjustable in elevation.

The upper part 1 is displaceable parallel to the base plate 4 with the aid of an adjusting lever 5 for aligning and for focussing the laser beam. A supply block is arranged below the base plate 4 and contains the following: a laser, a photomultiplier and an electronic signal processor. A first flexible and single-mode light-wave conductor 7 conducts the light transmitted by the laser to the upper part 1 of the apparatus. A second multimode and likewise flexible light-wave conductor 8 conducts the light of the viewing beam path to the photomultiplier.

The supply block 6 can contain several lasers of different wavelengths to provide color representations. The light beams corresponding to the different wavelengths can be coupled into the first light-wave conductor 7.

It is not necessary to mount the supply block 6 below the base plate 4. Instead, the supply block can be also disposed several meters away from the upper part 1 of the apparatus.

Figure 2:
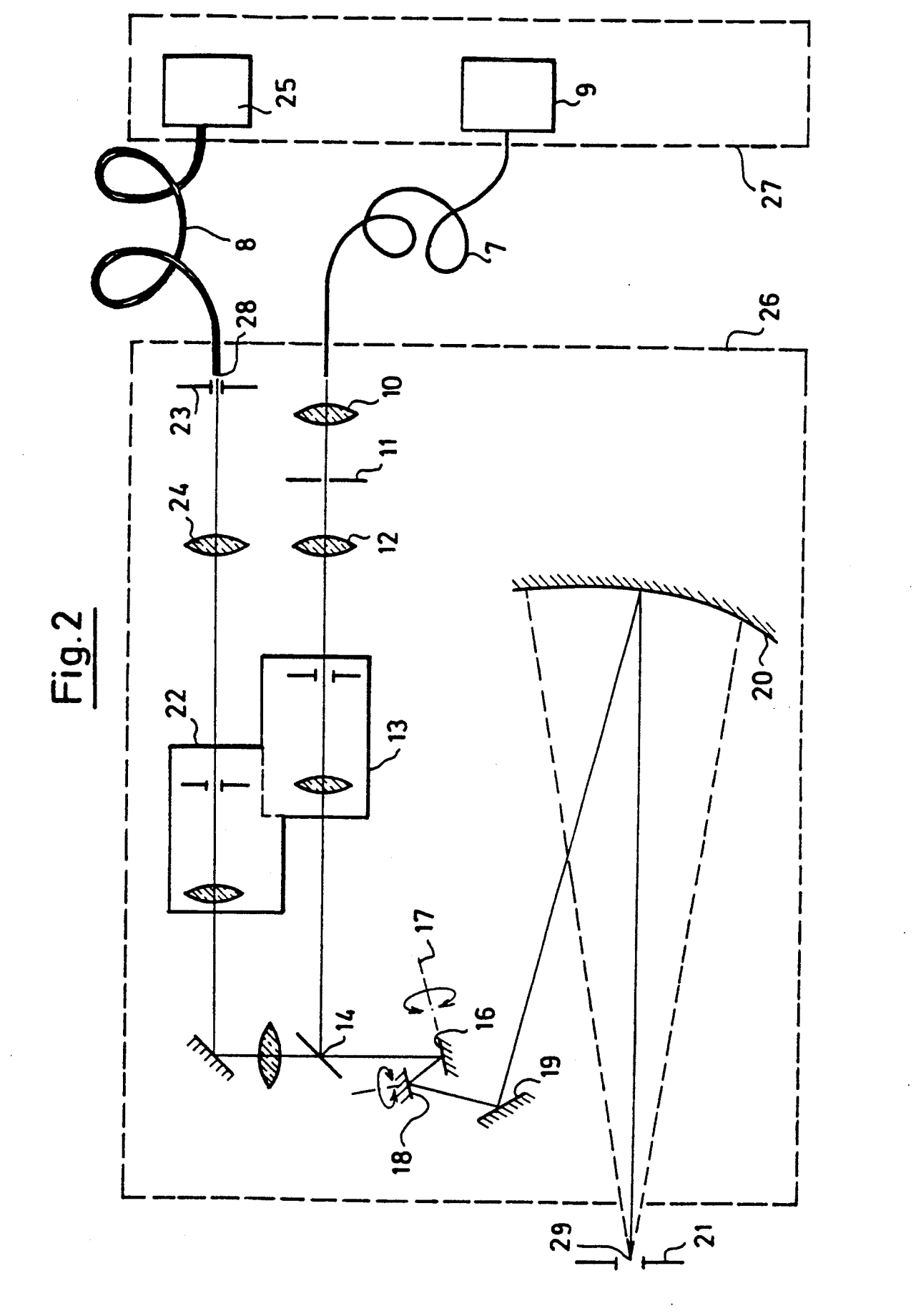

Only a single laser 9 is shown in the schematic of FIG. 2. The light of this laser 9 is conducted to the objective 10 via a light-wave conductor 7. The light-wave conductor 7 is a single-mode light-wave conductor having a core diameter of approximately 6 µm. The light conducted to the objective 10 is focussed into the plane 11 by this objective 10. The laser focus disposed in the plane 11 constitutes a point light source.

A second objective 12 collects the light of this point light source and conducts the same via a device 13 and a beam splitter 14 to a light-deflecting device. The device 13 functions to compensate for the ametropia of the patient. The light-deflecting device comprises a mirror-wheel scanner 16 rotating about the axis 17 and a galvano scanner 18. The mirror-wheel scanner 16 deflects the light perpendicularly to the plane of the drawing whereas the galvano scanner 18 deflects the light into the plane of the paper so that the laser beam scans the plane which lies perpendicularly to its direction of propagation.

Downstream of this light-deflecting device, the light is focussed on the ocular fundus of the patient via a deflecting mirror 19 and a concave mirror 20. The ocular fundus is here represented as an aperture 21. The deflection of the light beam by the mirror-wheel scanner 16 and the galvano scanner 18 effects a point-by-point scanning of the ocular fundus.

The light reflected from the ocular fundus is again collected by the concave mirror 20 and passes through the light-deflecting device in the opposite direction via the deflecting mirror 19. The beam splitter 14 then deflects this back-reflected light out of the common part of the illuminating and viewing beam path. A further device 22 corresponds to the device for compensating for the ametropia of the patient and is coupled therewith. After passing through the device 22, a third objective 24 generates an image of the laser focus 29 generated by the concave mirror 20. The image of the laser focus 29 is generated by the third objective 24 in the plane of the pinhole diaphragm 23.

The diameter of the pinhole diaphragm 23 is selected so that only the light of the laser focus 29 and thereby the light reflected at the ocular fundus is transmitted through the pinhole diaphragm 23. In contrast, the light scattered or reflected ahead of or behind the laser focus 29 is absorbed by the pinhole diaphragm 23. The pinhole diaphragm 23 therefore provides improved contrast and resolution.

With respect to the invention, it is decisive that the light transmitted through the pinhole diaphragm 23 is coupled into a flexible multimode light-wave conductor 8. An adjustment in the region of the pinhole diaphragm 23 is relatively non-critical because the multimode light-wave conductor 8 has a core diameter of approximately 0.3 mm. Movements of the multimode light-wave conductor 8 can cause transmission losses in this light-wave conductor 8. To prevent this transmission loss, the objective 24 is so selected that the numerical aperture of the multimode light-wave conductor has a value between 0.1 and 0.5.

The multimode light-wave conductor 8 conducts the light transmitted through the pinhole diaphragm 23 to a photomultiplier 25. The output signal of the photomultiplier 25 is conducted to an image memory (not shown) and a monitor (not shown). The monitor is synchronized with the light-deflecting device comprising the mirror-wheel scanner 16 and the galvano scanner 18. In this way, an image of the ocular fundus is displayed by the monitor.

By using two light-wave conductors (7, 8), the laser 9 as well as the photomultiplier 25 are spatially separated from the upper part 26 of the apparatus enclosed by the broken line. This separation can amount to several meters depending upon the length of the two light-wave conductors (7, 8). This spatial separation prevents interference of the electromagnetic stray fields emanating from the light-deflecting device into the output signal of the photomultiplier 25.

The flexibility of the two light-wave conductors (7, 8) makes possible an alignment of the upper part 26 of the apparatus and thereby of the laser focus 24 onto the ocular fundus of the patient; whereas, the laser 9 as well as the photomultiplier 25 are stationary. The photomultiplier 25 and the laser 9 are mounted in a common apparatus block 27 enclosed by a broken line.

A very compact configuration of this upper part of the apparatus is possible because the upper part 26 of the apparatus to be aligned with the eye of the patient contains neither the laser 9 nor a photomultiplier 25. This compact configuration makes it possible for the person conducting the examination to have a free view of the eye of the patient whereby a rapid and reliable alignment of the upper part 26 of the apparatus is possible.

The core of the multimode light-wave conductor 8 can replace the pinhole diaphragm 23 if the core diameter of the multimode light-wave conductor 8 corresponds to the diameter of the pinhole diaphragm 23. In this case, the end face 28 of the light-wave conductor 8 is to be positioned precisely in the plane of the pinhole diaphragm 23.

It is understood that the foregoing description is that of the preferred embodiments of the invention and that various changes and modifications may be made thereto without departing from the spirit and scope of the invention as defined in the appended claims.

What is claimed is:

1. A confocal scanning ophthalmoscope apparatus defining an illuminating beam path and a viewing beam path with respective portions of the paths extending along a common path segment, the ophthalmoscope apparatus comprising:
   a first apparatus part;
   a second apparatus part separate from said first apparatus part so as to permit movement of said parts relative to each other;
   a real light source for generating light for travelling along said illuminating beam path;
   focussing means for forming a point light source in said first apparatus part;
   a first flexible light-wave conductor for transmitting said light from said real light source to said focussing means;
   a light-deflecting device mounted in said first apparatus part on said common path segment to receive the light from said point light source for scanning the ocular fundus of a patient point-by-point and for transmitting light reflected from the ocular fundus;
   a pinhole diaphragm mounted in said viewing beam path in a plane conjugated to said point light source;
   means for transmitting the light reflected from the ocular fundus along said viewing beam path toward said pinhole diaphragm;
   a detector mounted in said second apparatus part for measuring the light transmitted through said pinhole diaphragm; and,
   a second flexible light-wave conductor disposed between said pinhole diaphragm and said detector for conducting the light transmitted through said pinhole diaphragm to said detector.

2. The confocal scanning ophthalmoscope apparatus of claim 1, said second flexible light-wave conductor being a multimode light-wave conductor.

3. The confocal scanning ophthalmoscope apparatus of claim 2, said real light source also being mounted in said second apparatus part.

4. The confocal scanning ophthalmoscope apparatus of claim 3, said detector being a photomultiplier.

5. The confocal scanning ophthalmoscope apparatus of claim 2, said pinhole diaphragm defining an aperture having a diameter; and, said second flexible light-wave conductor having a core diameter greater than said diameter of said aperture.

6. The confocal scanning ophthalmoscope apparatus of claim 2, said second flexible light-wave conductor being dimensioned so as to constitute said pinhole diaphragm.

* * * * *